(12) United States Patent
Singh et al.

(10) Patent No.: US 11,464,529 B2
(45) Date of Patent: *Oct. 11, 2022

(54) SYSTEMS AND METHODS TO MODIFY INTRAVASCULAR LESIONS

(71) Applicant: C. R. Bard, Inc., Franklin Lakes, NJ (US)

(72) Inventors: Aseem Singh, Tempe, AZ (US); Peng Zheng, Chandler, AZ (US); Chad Van Liere, Phoenix, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 336 days.

This patent is subject to a terminal disclaimer.

(21) Appl. No.: 16/437,138

(22) Filed: Jun. 11, 2019

(65) Prior Publication Data

US 2019/0290303 A1 Sep. 26, 2019

Related U.S. Application Data

(63) Continuation of application No. 15/351,208, filed on Nov. 14, 2016, now Pat. No. 10,357,262.

(51) Int. Cl.
| | |
|---|---|
| *A61B 17/22* | (2006.01) |
| *A61M 25/09* | (2006.01) |
| *A61M 25/00* | (2006.01) |
| *A61B 17/32* | (2006.01) |

(Continued)

(52) U.S. Cl.
CPC .... *A61B 17/2202* (2013.01); *A61B 17/22012* (2013.01); *A61B 17/320068* (2013.01); *A61M 25/005* (2013.01); *A61M 25/09041* (2013.01); *A61B 2017/00154* (2013.01); *A61B 2017/00172* (2013.01); *A61B 2017/00194* (2013.01); *A61B 2017/22014* (2013.01); *A61B 2017/22018* (2013.01); *A61B 2017/2948* (2013.01); *A61B 2017/320069* (2017.08); *A61B 2017/320088* (2013.01); *A61B 2017/320098* (2017.08); *B06B 2201/76* (2013.01)

(58) Field of Classification Search
CPC ........ A61B 17/2202; A61B 17/320068; A61B 2017/320069; A61B 2017/00154; A61M 25/09041; A61M 25/005; B06B 2201/76
See application file for complete search history.

(56) References Cited

U.S. PATENT DOCUMENTS

| | | | |
|---|---|---|---|
| 5,304,115 A | * | 4/1994 | Pflueger ........... A61B 17/22012 604/22 |
| 5,989,208 A | | 11/1999 | Nita |
| 5,997,497 A | | 12/1999 | Nita et al. |

(Continued)

*Primary Examiner* — Julian W Woo
(74) *Attorney, Agent, or Firm* — Dinsmore & Shohl LLP

(57) ABSTRACT

An ultrasonic catheter assembly includes a sheath having a sheath lumen. A core wire is at least partially disposed within the sheath lumen. The core wire has a proximal portion and a distal portion. The proximal portion of the core wire is configured to be coupled to an ultrasound-producing mechanism. A working length of the distal portion of the core wire extends distally from the sheath. The working length is configured for longitudinal displacement, transverse displacement, or a combination of longitudinal and transverse displacement, in accordance with a plurality of output modes for vibrational energy supplied to the core wire proximal portion by the ultrasound-producing mechanism.

18 Claims, 8 Drawing Sheets

Figure 1:
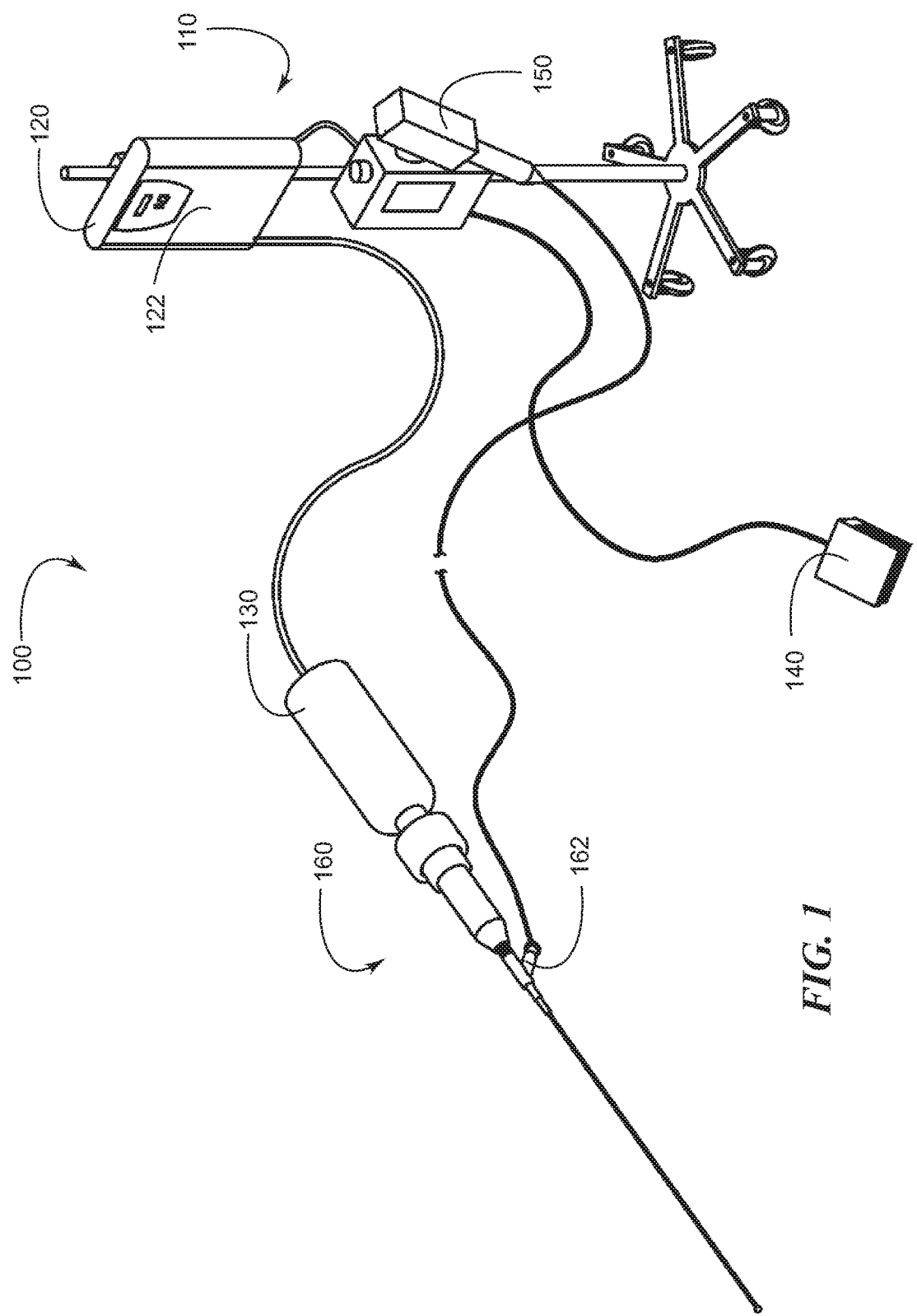

(51) Int. Cl.
    *A61B 17/00*        (2006.01)
    *A61B 17/29*        (2006.01)

(56) References Cited

U.S. PATENT DOCUMENTS

| | | | |
|---|---|---|---|
| 6,027,515 | A | 2/2000 | Cimino |
| 6,450,975 | B1 * | 9/2002 | Brennan .......... A61B 17/22012 |
| | | | 600/585 |
| 6,733,451 | B2 | 5/2004 | Rabiner et al. |
| 7,431,728 | B2 | 10/2008 | Gerry et al. |
| 7,494,468 | B2 | 2/2009 | Rabiner et al. |
| 7,534,249 | B2 | 5/2009 | Nash et al. |
| 8,323,240 | B2 | 12/2012 | Wulfman et al. |
| 8,556,813 | B2 | 10/2013 | Cioanta et al. |
| 8,647,293 | B2 | 2/2014 | Nita |
| 9,014,786 | B2 | 4/2015 | Carmeli et al. |
| 9,161,768 | B2 | 10/2015 | Cioanta et al. |
| 10,357,262 | B2 * | 7/2019 | Singh .............. A61M 25/09041 |
| 10,893,883 | B2 * | 1/2021 | Dannaher ...... A61B 17/320068 |
| 2005/0273123 | A1 | 12/2005 | Dongelmans |
| 2006/0241523 | A1 | 10/2006 | Sinelnikov et al. |
| 2007/0066978 | A1 | 3/2007 | Schafer et al. |
| 2007/0250001 | A1 | 10/2007 | Hilaire et al. |
| 2008/0171965 | A1 | 7/2008 | Soltani et al. |
| 2011/0196397 | A1 | 8/2011 | Frantz et al. |
| 2013/0023897 | A1 | 1/2013 | Wallace |
| 2013/0072824 | A1 | 3/2013 | Nita et al. |
| 2013/0267875 | A1 | 10/2013 | Thapliyal et al. |
| 2014/0022046 | A1 | 1/2014 | Saimoto et al. |
| 2015/0073391 | A1 | 3/2015 | Hutchins et al. |

* cited by examiner

SYSTEMS AND METHODS TO MODIFY INTRAVASCULAR LESIONS

PRIORITY

This is a continuation of U.S. patent application Ser. No. 15/351,208, filed Nov. 14, 2016, now U.S. Pat. No. 10,357,262, which is hereby incorporated by reference in its entirety.

FIELD

This application generally relates to systems and methods for modifying intravascular lesions.

BACKGROUND

Atherosclerosis is characterized by one or more intravascular lesions formed in part of plaque including blood-borne substances such as fat, cholesterol, and calcium. An intravascular lesion such as an arterial lesion can form on a side of an arterial lumen and build out across the lumen to an opposite side thereof. A last point of patency often occurs at a boundary between the arterial lesion and the opposite side of the arterial lumen.

Surgical procedures for atherosclerosis such as atherectomy and angioplasty can be used to restore patency and blood flow lost to the one or more intravascular lesions; however, a number of different devices are needed to perform any one of the surgical procedures. For example, atherectomy can involve placing a guidewire through an intravascular lesion with a first, lesion-crossing device and subsequently advancing a second, atherectomy device to the lesion for ablation thereof. Each of a number of different devices needs to be inserted into and removed from a patient, thereby increasing a risk of surgical complication. Accordingly, there is a need to reduce the number of different devices used for surgical procedures for atherosclerosis. Provided herein in some embodiments are systems and methods that address the foregoing.

SUMMARY

Provided herein in some embodiments is a system including a console and a catheter assembly. The console includes an ultrasound-producing mechanism configured to convert an electric current into a vibrational energy. The console also includes a driving-parameter modifier configured to modify driving parameters to selectively provide one or more output modes for the vibrational energy. The catheter assembly includes a sheath including a sheath lumen and a core wire at least partially disposed within the sheath lumen. The core wire includes a proximal portion and a distal portion of the core wire, wherein the proximal portion of the core wire is coupled to the ultrasound-producing mechanism. A working length of the distal portion of the core wire beyond the sheath is configured for longitudinal, transverse, or longitudinal and transverse displacement in accordance with the one or more output modes for the vibrational energy to effect different intravascular lesion-modification procedures.

These and other features of the concepts provided herein may be better understood with reference to the drawings, description, and appended claims.

DRAWINGS

FIG. 1 provides a schematic illustrating a system in accordance with some embodiments.

Figure 2:
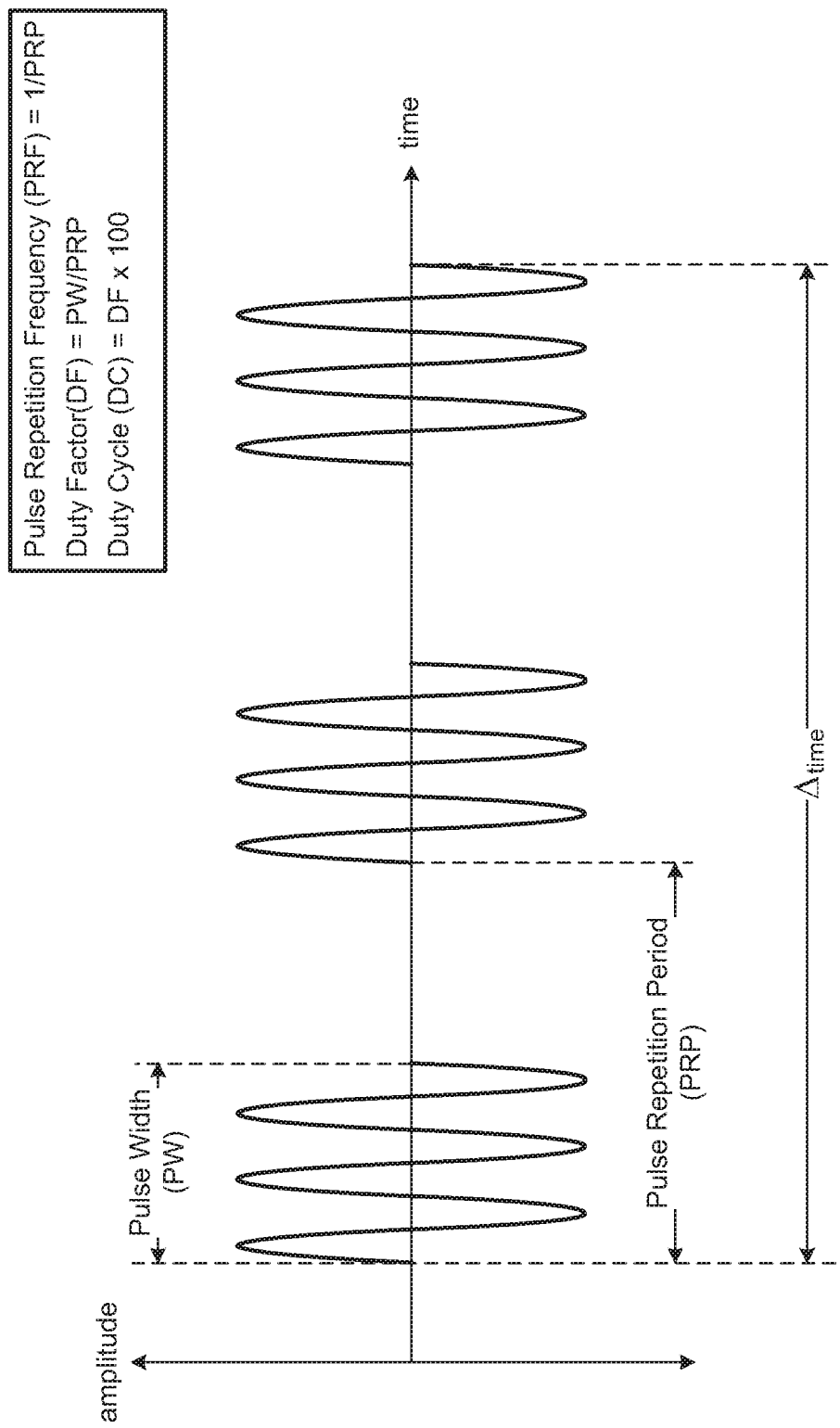

FIG. 2 provides a graph illustrating pulse repetition frequency and duty cycle driving parameters in accordance with some embodiments.

Figure 3:
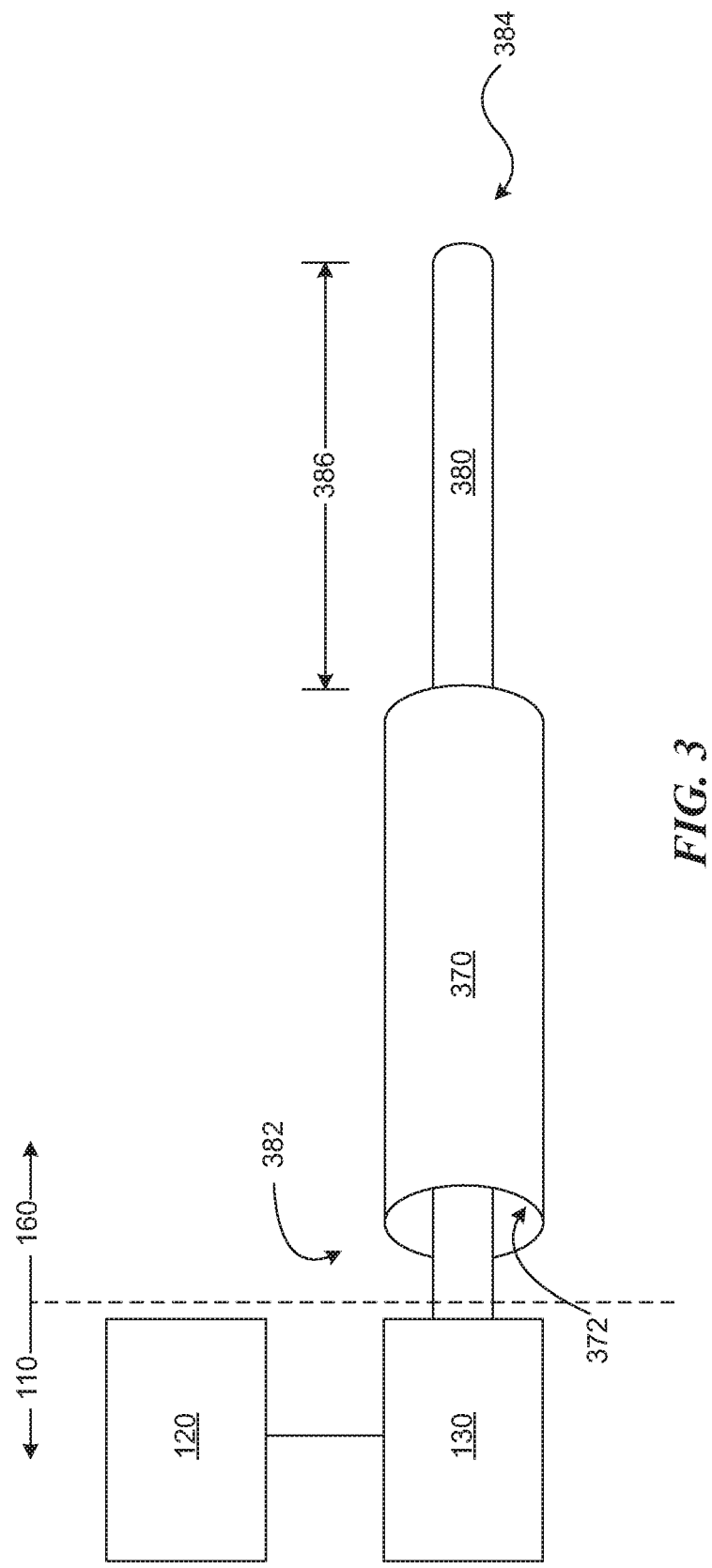

FIG. 3 provides a schematic illustrating a catheter assembly of a system in accordance with some embodiments.

Figure 4A:
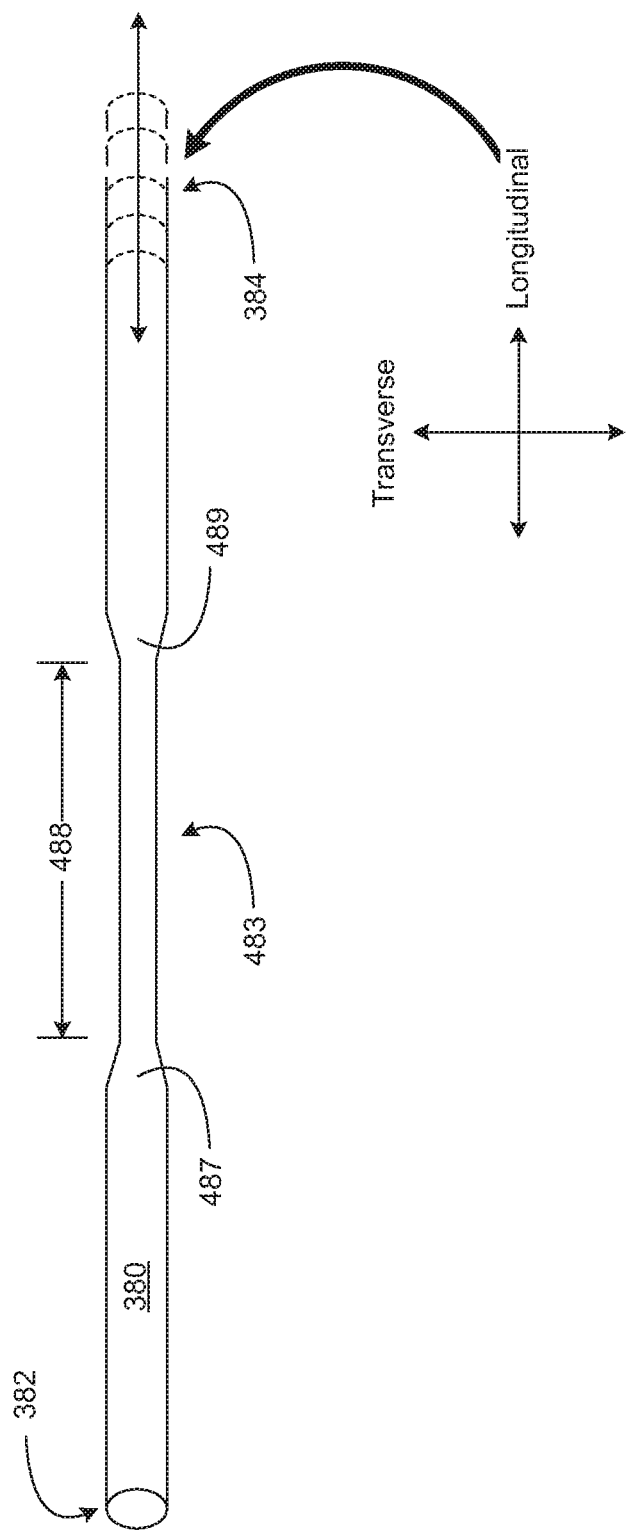

FIG. 4A provides a schematic illustrating a buckling section of a core wire of a catheter assembly in accordance with some embodiments.

Figure 4B:
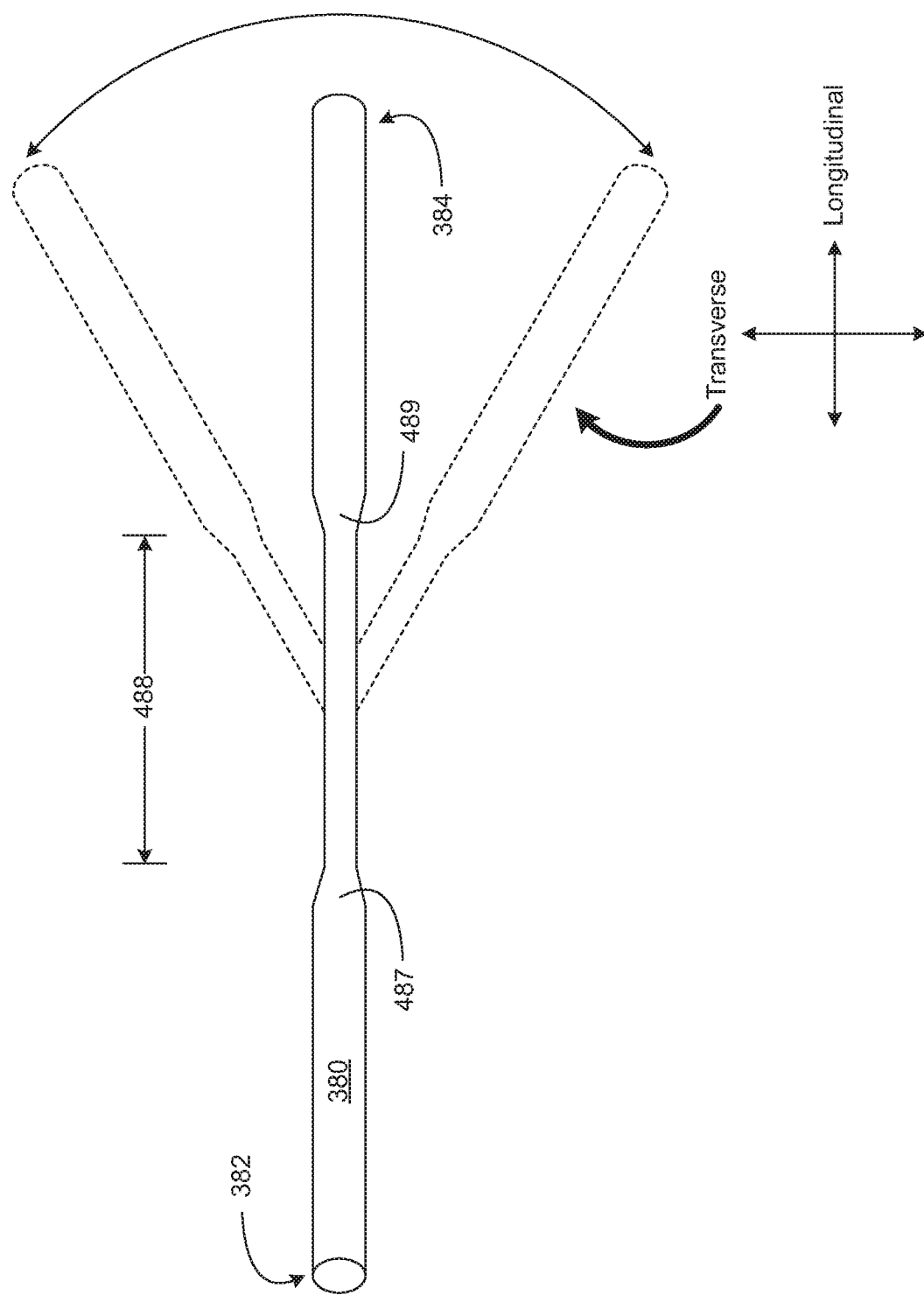

FIG. 4B provides a schematic illustrating a buckling section of a core wire of a catheter assembly in accordance with some embodiments.

Figure 5A:
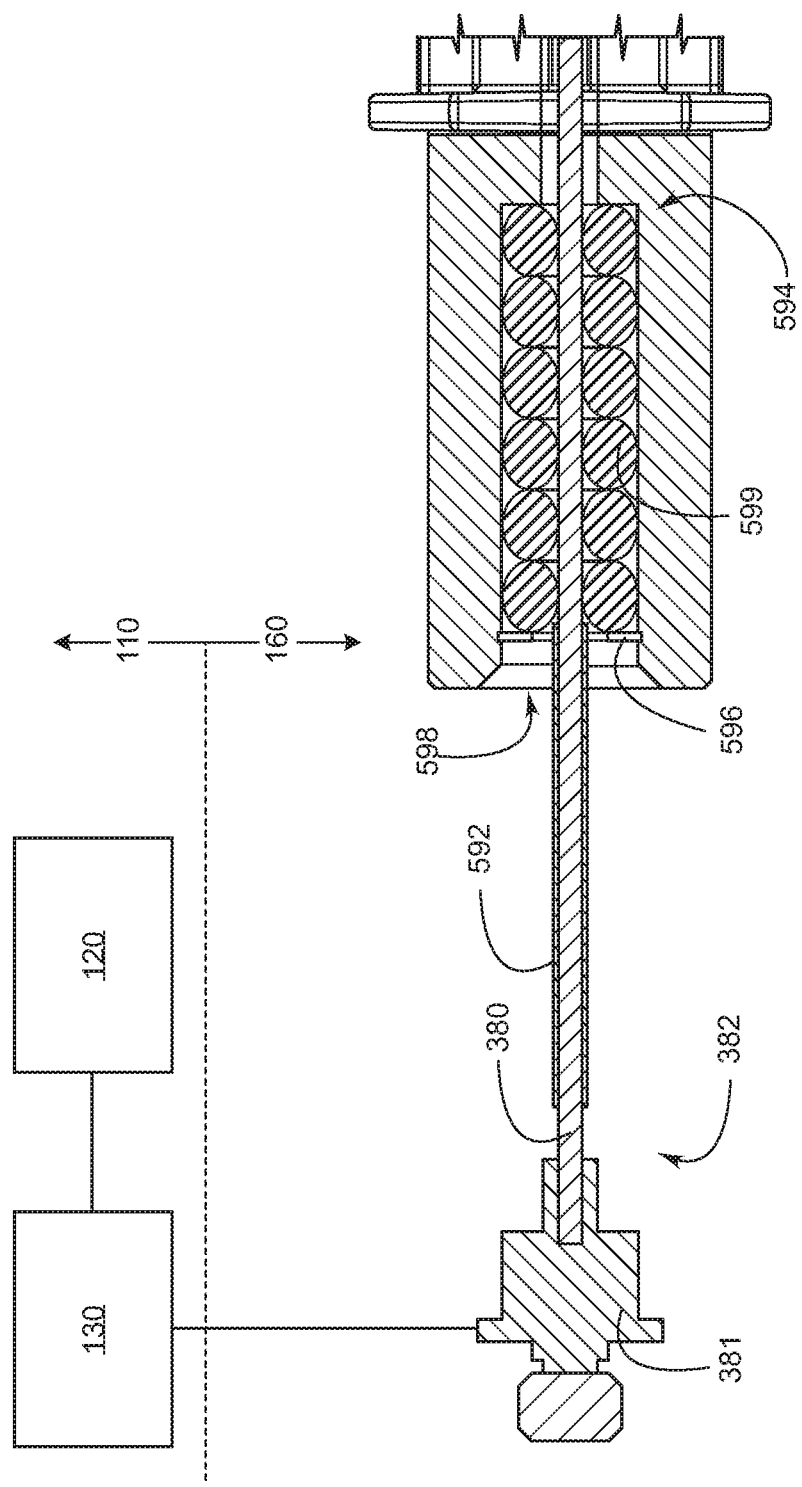

FIG. 5A provides a schematic illustrating a damping mechanism of a catheter assembly in accordance with some embodiments.

Figure 5B:
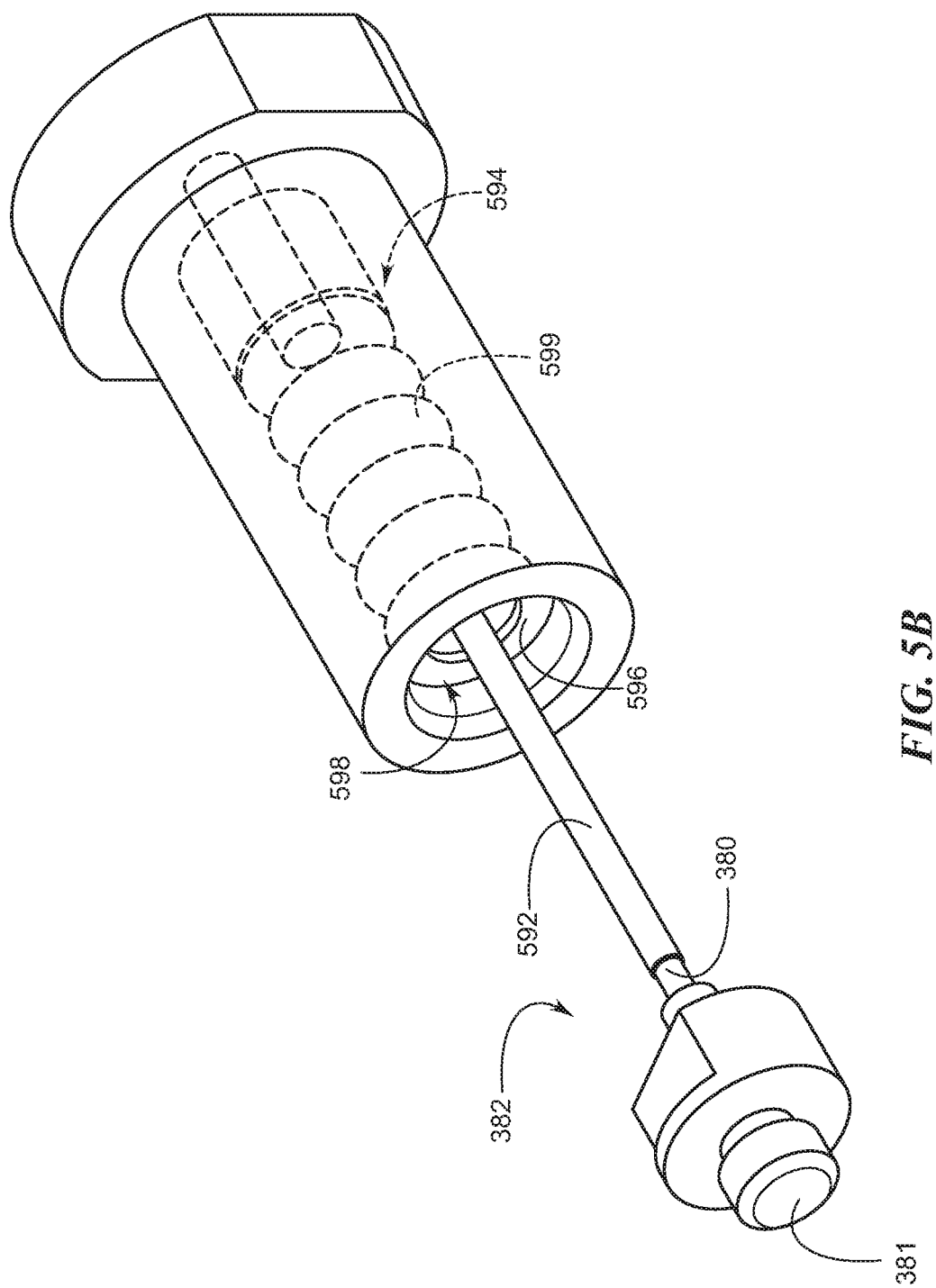

FIG. 5B provides a schematic illustrating a damping mechanism of a catheter assembly in accordance with some embodiments.

Figure 6:
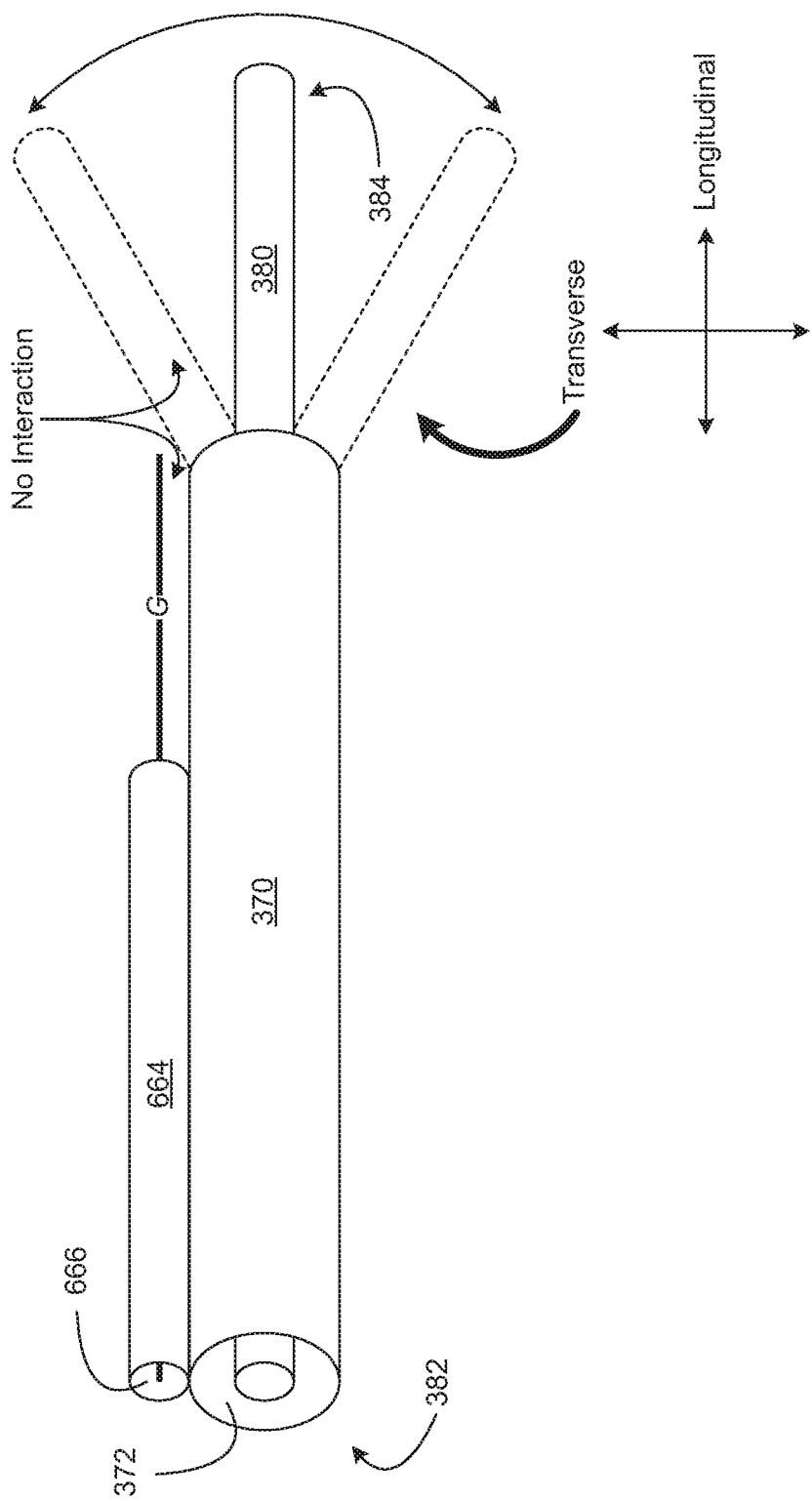

FIG. 6 provides a schematic illustrating a guidewire rail of a catheter assembly in accordance with some embodiments.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood to those of ordinary skill in the art.

Atherosclerosis is characterized by one or more intravascular lesions formed in part of plaque including blood-borne substances such as fat, cholesterol, and calcium. Surgical procedures for atherosclerosis such as atherectomy and angioplasty can be used to restore patency and blood flow lost to the one or more intravascular lesions; however, a number of different devices are needed to perform any one of the surgical procedures. For example, atherectomy can involve placing a guidewire through an intravascular lesion with a first, lesion-crossing device and subsequently advancing a second, atherectomy device to the lesion for ablation thereof. Each of the number of different devices needs to be inserted into and removed from a patient, thereby increasing a risk of surgical complication. Accordingly, there is a need to reduce the number of different devices used for surgical procedures for atherosclerosis. Provided herein in some embodiments are systems and methods that address the foregoing.

For example, provided herein in some embodiments is a system including a console and a catheter assembly. The console includes an ultrasound-producing mechanism configured to convert an electric current into a vibrational energy. The console also includes a driving-parameter modifier configured to modify driving parameters to selectively provide one or more output modes for the vibrational energy. The catheter assembly includes a sheath including a sheath lumen and a core wire at least partially disposed within the sheath lumen. The core wire includes a proximal portion and a distal portion of the core wire, wherein the proximal portion of the core wire is coupled to the ultrasound-producing mechanism. A working length of the distal portion of the core wire beyond the sheath is configured for longitudinal, transverse, or longitudinal and transverse displacement in accordance with the one or more output modes for the vibrational energy to effect different intravascular lesion-modification procedures.

In some embodiments, the one or more output modes include at least an atherectomy mode and a crossing mode to respectively ablate and cross intravascular lesions. Each of the atherectomy mode and the crossing mode, in turn, can include one or more output modes thereof.

FIG. 1 provides a schematic illustrating a system 100 in accordance with some embodiments. As shown, the system 100 can include a console 110 and a catheter assembly 160.

Console

The console 110 provides a system operator an instrument for monitoring and controlling the system and various sub-systems and functions thereof. The console 110 can include an ultrasound-producing mechanism including an ultrasound generator 120 and an ultrasound transducer 130. The ultrasound-producing mechanism can be configured to convert an electric current into a vibrational energy. For example, the ultrasound generator 120 can be configured to convert an alternating electric current (e.g., a current associated with mains electricity) into a high-frequency current (e.g., a current with a frequency commensurate with the operating frequency of the ultrasound transducer 130), and the ultrasound transducer 130, in turn, can be configured to convert the high-frequency current into the vibrational energy (e.g., >20 kHz such as 20.5 kHz±500 Hz). The console 110 can also include a driving-parameter modifier 122 configured to modify driving parameters to selectively provide one or more output modes for the vibrational energy. The one or more output modes for the vibrational energy can effect different intravascular lesion-modification procedures with the core wire of the catheter assembly 160. The core wire can be configured for longitudinal, transverse, or longitudinal and transverse displacement at a distal end of the core wire in accordance with one or more output modes for the vibrational energy.

In some embodiments, the console 110 can further include a foot switch 140 configured to activate and deactivate the system such as activate and deactivate the core wire of the catheter assembly 160. For example, when the system 100 is powered on but not activated, the foot switch 140 can be used to activate the system 100, thereby activating the core wire of the catheter assembly 160. When the system 100 is powered on and activated, the foot switch 140 can be used to deactivate the system 100, thereby deactivating the core wire of the catheter assembly 160. In some embodiments, the console 110 can further include an injector 150 configured to inject an irrigant into an optional irrigation lumen 162 of the catheter assembly 160. The irrigant can be, for example, sterile saline for irrigating an anatomical area undergoing an intravascular lesion-modification procedure, cooling the core wire of the catheter assembly, or a combination thereof. In some embodiments, the console 110 can further include the foot switch 140 and the injector 150. In such embodiments, the foot switch 140 can be further configured to activate and deactivate the injector 150 when the system 100 is respectively activated and deactivated with the foot switch 140.

The driving-parameter modifier 122 can be configured to modify any of a number of drive parameters including, but not limited to, at least the driving parameters selected from pulse repetition frequency, duty cycle, and a combination of the pulse repetition frequency and the duty cycle to effect the different intravascular lesion-modification procedures. The driving-parameter modifier 122 can include any of a number of controls including, but not limited to, buttons, switches, knobs, wheels, or a combination thereof for a system operator to switch between the atherectomy mode and the crossing mode, modify any of the number of drive parameters, or a combination thereof.

FIG. 2 provides a graph illustrating pulse repetition frequency and duty cycle driving parameters in accordance with some embodiments.

With respect to pulse repetition frequency, a number of pulses such as ultrasonic pulses from an ultrasound transducer can occur over a particular time interval $\Delta_{time}$ as shown in FIG. 2. Each pulse of the number of pulses can have a pulse width ("PW") measured in a unit of time such as a fraction of $\Delta_{time}$, and the time between the start of any two consecutive pulses can define a pulse repetition period ("PRP"). The pulse repetition frequency ("PRF") is the inverse of the pulse repetition period; that is, PRF=PRP$^{-1}$. When $\Delta_{time}$ is one second, for example, the pulse repetition frequency can be expressed in the number of pulses per second or Hz. FIG. 2 provides an example 3-Hz pulse repetition frequency for a 1-second $\Delta_{time}$.

With respect to duty cycle, the duty cycle is a duty factor expressed as a fraction of 100 (i.e., a percentage). The duty factor ("DF"), in turn, is a fraction of the pulse repetition period each pulse of the number of pulses is present during the pulse repetition period. Each pulse is considered present during the pulse repetition period over its pulse width. As such, DF=PW/PRP, and DC=DF×100. FIG. 2 provides an example duty factor of about 0.50 and duty cycle of about 50%.

The driving-parameter modifier 122 can be configured to modify the pulse repetition frequency to provide, for example, transverse displacement of the core wire at a sufficient amplitude to effect atherectomy procedures. A pulse repetition frequency between about 5 Hz and 25 Hz, including about 5 Hz and 17 Hz, such as about 5 Hz and 10 Hz, can provide the transverse displacement of the core wire at the sufficient amplitude to effect the atherectomy procedures. A duty cycle between about 50% and 75% for the pulse repetition frequency between about 5 Hz and 25 Hz can further provide the transverse displacement of the core wire at the sufficient amplitude to effect the atherectomy procedures. The duty cycle between about 50% and 75% for the pulse repetition frequency between about 5 Hz and 10 Hz can even further provide the transverse displacement of the core wire at the sufficient amplitude to effect the atherectomy procedures.

The driving-parameter modifier 122 can be configured to modify the duty cycle to provide, for example, longitudinal displacement of the core wire at a sufficient amplitude to effect intravascular lesion-crossing procedures. A duty cycle between about 25% and 100%, including about 50% and 100%, such as about 75% and 100%, can provide the longitudinal displacement of the core wire at the sufficient amplitude to effect the intravascular lesion-crossing procedures. A pulse repetition frequency between about 10 Hz and 25 Hz for the duty cycle between about 75% and 100% for can further provide the longitudinal displacement of the core wire at the sufficient amplitude to effect the intravascular lesion-crossing procedures. For a duty cycle of about 100%, pulse repetition frequency becomes a smaller component in providing the longitudinal displacement of the core wire at the sufficient amplitude to effect the intravascular lesion-crossing procedures. Any pulse repetition frequency including a pulse repetition frequency between about 5 Hz and 25 Hz for the duty cycle of about 100% can even further provide the longitudinal displacement of the core wire at the sufficient amplitude to effect the intravascular lesion-crossing procedures.

Dimensional and/or material modifications to the core wire of the catheter assembly 160 can affect the pulse repetition frequency and the duty cycle for effecting the different intravascular lesion-modification procedures. As such, it should be understood that the driving-parameter modifier 122 is not limited in its configuration to modify the pulse repetition frequency in the foregoing 5-25 Hz range. In some embodiments, the driving-parameter modifier 122 can be further configured to modify the pulse repetition frequency to less than about 5 Hz, greater than about 25 Hz, or less than about 5 Hz and greater than about 25 Hz. It should also be understood that the driving-parameter modifier 122 is not limited in its configuration to modify the duty cycle in the foregoing 25-100% range. In some embodiments, the driving-parameter modifier 122 can be further configured to modify the duty cycle to less than about 25%.

Catheter Assembly

FIG. 3 provides a schematic illustrating a catheter assembly 160 of the system 100 in accordance with some embodiments.

The catheter assembly 160 can include a sheath 370 including a sheath lumen 372 and a core wire 380 at least partially disposed within the sheath lumen 372. The core wire 380 can include a proximal portion 382 and a distal portion 384 of the core wire, wherein the proximal portion 382 of the core wire 380 can be coupled to the ultrasound-producing mechanism by a sonic connector 381 (see FIGS. 5A and 5B) to the ultrasound transducer 130 or an intervening ultrasonic horn. A working length 386 of the distal portion 384 of the core wire 380 beyond the sheath 370 can be configured for displacement in accordance with the one or more output modes for the vibrational energy to effect different intravascular lesion-modification procedures. The working length 386 of the core wire 380 can range between about 5 and 200 mm, including about 5 and 100 mm or 100 and 200 mm.

The working length 386 of the core wire 380 can be configured for longitudinal, transverse, or longitudinal and transverse displacement in accordance with the one or more output modes for the vibrational energy including the crossing mode and the atherectomy mode. Longitudinal displacement of the working length 386 of the core wire 380 can result in micromotion such as cavitation, and transverse displacement of the working length 386 of the core wire 380 can result in macromotion. In the crossing mode, the micromotion can be used to cross intravascular lesions. In the atherectomy mode, the macromotion coupled with the micromotion can be used to ablate intravascular lesions, thereby breaking the lesions into minute fragments and restoring patency and blood flow.

The core wire 380 can be configured without a tip, thereby eliminating surgical procedure-based complications resulting from tip breakage such as tip separation from the core wire 380. To further eliminate surgical procedure-based complications, the core wire 380 can be bulked up in the distal portion 384 such as at a distal end of the core wire 380 to provide a more durable distal portion 384, thereby mitigating surgical procedure-based wire breakage in the distal portion 384 of the core wire 380. A bulked-up distal portion 384 of the core wire 380 includes an increased mass in the distal portion 384 of the core wire compared to tapered core wires. The increased mass can result from an increased size of the distal portion 384 of the core wire, an increased density of the distal portion 384 of the core wire, or a combination thereof. In addition to mitigating surgical procedure-based wire breakage in the distal portion 384 of the core wire 380, the bulked-up distal portion 384 of the core wire can provide an anchor and a nodal location for producing longitudinal displacement in the core wire 380.

FIGS. 4A and 4B provide schematics illustrating a buckling section of a core wire of a catheter assembly in accordance with some embodiments.

In some embodiments, the core wire 380 can include a buckling section 488 configured to produce transverse displacement in the working length of the core wire 380 by buckling in accordance with the one or more output modes for the vibrational energy. The buckling section 488 can be within a medial portion 483 of the core wire 380 between the proximal portion 382 and the distal portion 384 of the core wire. The medial portion 483 of the core wire 380 can include a tapered section 487 and an inversely tapered section 489 of the core wire 380, and the buckling section 488 can be between the tapered section 487 and the inversely tapered section 489 with a cross-sectional area smaller than either one of the tapered section 487 or the inversely tapered section 489. The buckling section 488 can be at least about 1" long, including at least about 2" long, such as at least about 3" long, for example, at least about 4" long. In some embodiments, the buckling section can be about 3-4" long.

FIGS. 5A and 5B provide schematics illustrating a damping mechanism of a catheter assembly in accordance with some embodiments.

The catheter assembly 160 can include a damping mechanism about the proximal portion 382 of the core wire 380 configured to dampen transversely oriented vibrational energy in favor of longitudinally oriented vibrational energy about the proximal portion 382 of the core wire 380, as well as prevent fatigue of the core wire 380. The damping mechanism can include a sleeve 592 encasing the core wire 380 with a first radial compressive force; a gasket system 594 encasing the sleeve 592 with a second radial compressive force; and a retainer 596 configured to retain the gasket system 594 within a damping-mechanism bore 598 of the catheter assembly 160. The sleeve 592 encasing the core wire 380 can be a polymeric sleeve 592 such as a polytetrafluoroethylene ("PTFE") sleeve 592. The first radial compressive force of the sleeve 592 on the core wire 380 can range from that associated with an engineering fit selected from a clearance fit, a transition fit, and an interference fit.

The clearance fit is a fairly loose fit that enables the core wire 380 to freely rotate or slide within the sleeve 592; the transition fit firmly holds the core wire 380 in place within the sleeve 592, but not so firmly that the core wire 380 cannot be removed from the sleeve 592; and the interference fit securely holds the core wire 380 in place within the sleeve 592 such that the core wire 380 cannot be removed from the sleeve 592 without damaging the core wire 380, the sleeve 592, or both the core wire 380 and the sleeve 592. In some embodiments, the first radial compressive force of the sleeve 592 on the core wire 380 is associated with a transition fit or an interference fit. The transition fit and the interference fit can be effected by, for example, heat-shrinking a suitably sized PTFE for the desired fit about the core wire 380 during assembly of the catheter assembly 160.

The gasket system 594 can include a number of O-rings 599. The number of O-rings 599 can range from 1 O-ring to 12 O-rings, including 2 O-rings, such as 4 O-rings, for example, 6 O-rings. The O-rings 599 can be compressed in the damping-mechanism bore 598 of the catheter assembly 160 and retained in the damping-mechanism bore 598 with a longitudinal compression by the retainer 596, for example, a washer. The longitudinal compression contributes to a radial compression on the core wire 380 sufficient to dampen transversely oriented vibrational energy in favor of longitudinally oriented vibrational energy about the proximal portion 382 of the core wire 380. The damping mechanism can be centered over a vibrational node of the core wire 380 to minimize frictional heating caused by damping the transversely oriented vibrational energy. Minimized frictional heating obviates a need for a heat sink in the damping mechanism of the catheter assembly 160. In embodiments of the system 100 including the injector 150, the gasket system 594 can prevent irrigation backflow of the irrigant through the catheter assembly 160 and into the ultrasound-producing mechanism.

FIG. 6 provides a schematic illustrating a guidewire rail of a catheter assembly in accordance with some embodiments.

The catheter assembly 160 can further include a guidewire rail 664 comprising a guidewire-rail lumen 666 externally fixed to the sheath 370 such as side-by-side with the sheath 370. The guidewire rail 664 can terminate about a distal sheath terminus where the working length of the core wire 380 is free to transversely displace without interacting with the guidewire rail 664, a guidewire G wholly or partially disposed within the guidewire-rail lumen 666, or a combination of the guidewire rail 664 and the guidewire G. Thus, subtleties associated with drive parameter modifications (e.g., modification of the pulse repetition frequency, the duty cycle, etc.) for the one or more output modes of the vibrational energy are not affected.

EXAMPLE

A system in accordance with some embodiments was used to modify the drive parameters including the pulse repetition frequency and the duty cycle to determine values therefor for effecting at least the atherectomy mode and the crossing mode. The efficacy of the atherectomy mode and the crossing mode to respectively ablate and cross intravascular lesions was also qualitatively determined. With respect to the atherectomy output mode, it was determined that a pulse repetition frequency between about 5 Hz and 10 Hz and a duty cycle between about 50% and 75% can provide the transverse displacement of the core wire at a sufficient amplitude to effect the atherectomy procedures. Table 1 provides some of the drive parameters from which the foregoing was determined.

TABLE 1

Atherectomy output modes for a number of pulse repetition frequency and duty cycle driving parameters ordered by increasing pulse repetition frequency

| Output mode (atherectomy) | PRF (Hz) | DC (%) |
| --- | --- | --- |
| 1 | 5 | 25 |
| 2 | 5 | 50 |
| 3 | 5 | 75 |
| 4 | 10 | 25 |
| 5 | 10 | 50 |
| 6 | 10 | 75 |
| 7 | 10 | 100 |
| 8 | 17 | 50 |
| 9 | 25 | 50 |

With respect to the crossing output mode, it was determined that a pulse repetition frequency between about 10 Hz and 25 Hz for a duty cycle between about 75% and 100% can provide the longitudinal displacement of the core wire at the sufficient amplitude to effect the lesion-crossing procedures. The pulse repetition frequency becomes a smaller component in providing the longitudinal displacement of the core wire at the sufficient amplitude to effect the intravascular lesion-crossing procedures for a duty cycle of about 100%. Any pulse repetition frequency including a pulse repetition frequency between about 5 Hz and 25 Hz for the duty cycle of about 100% can provide the longitudinal displacement of the core wire at the sufficient amplitude to effect the intravascular lesion-crossing procedures. Table 2 provides some of the drive parameters from which the foregoing was determined.

TABLE 2

Crossing output modes for a number of pulse repetition frequency and duty cycle driving parameters ordered by increasing pulse repetition frequency

| Output mode (crossing) | PRF (Hz) | DC (%) |
| --- | --- | --- |
| 1 | 5 | 50 |
| 2 | 10 | 50 |
| 3 | 10 | 75 |
| 4 | 17 | 50 |
| 5 | 17 | 75 |
| 6 | 25 | 50 |
| 7 | 25 | 75 |
| 8 | any | 100 |

As such, provided herein in some embodiments is a system including a console and a catheter assembly. The console includes an ultrasound-producing mechanism configured to convert an electric current into a vibrational energy. The console also includes a driving-parameter modifier configured to modify driving parameters to selectively provide one or more output modes for the vibrational energy. The catheter assembly includes a sheath including a sheath lumen and a core wire at least partially disposed within the sheath lumen. The core wire includes a proximal portion and a distal portion of the core wire, wherein the proximal portion of the core wire is coupled to the ultrasound-producing mechanism. A working length of the distal portion of the core wire beyond the sheath is configured for longitudinal, transverse, or longitudinal and transverse displacement in accordance with the one or more output modes for the vibrational energy to effect different intravascular lesion-modification procedures. In some embodiments, the driving-parameter modifier is configured to modify at least the driving parameters selected from pulse repetition frequency, duty cycle, and a combination of the pulse repetition frequency and the duty cycle to effect the different intravascular lesion-modification procedures. In some embodiments, the driving-parameter modifier is configured to modify the pulse repetition frequency between about 5 Hz and 10 Hz to provide transverse displacement of the core wire at a sufficient amplitude to effect atherectomy procedures. In some embodiments, the driving-parameter modifier is configured to modify the duty cycle between about 75% and 100% to provide longitudinal displacement of the core wire at a sufficient amplitude to effect intravascular lesion-crossing procedures.

In some embodiments, the core wire further includes a buckling section between the proximal portion and the distal portion of the core wire configured to produce transverse displacement in the working length of the core wire by buckling in accordance with the one or more output modes for the vibrational energy. In some embodiments, the catheter assembly further includes a damping mechanism about the proximal portion of the core wire configured to dampen transversely oriented vibrational energy in favor of longitudinally oriented vibrational energy about the proximal portion of the core wire. In some embodiments, the damping mechanism includes a sleeve encasing the core wire with a first radial compressive force; a gasket system encasing the sleeve with a second radial compressive force; and a washer configured to contain the gasket system within a damping-mechanism bore of the catheter assembly. In some embodiments, the catheter assembly further includes a guidewire rail including a guidewire-rail lumen externally fixed to the sheath, wherein the guidewire rail terminates about a distal sheath terminus where the guidewire rail, a guidewire disposed within the guidewire-rail lumen, or a combination of the guidewire rail and a guidewire disposed within the guidewire-rail lumen is free from any effects of transverse displacement of the working length of the core wire.

Also provided herein in some embodiments is a system including a console. The console includes an ultrasound generator, an ultrasound transducer, and a driving-parameter modifier. The ultrasound generator is configured to convert an alternating electric current into a high-frequency current. The ultrasound transducer is configured to convert the high-frequency current into a vibrational energy. The driving-parameter modifier is configured to modify driving parameters to selectively provide one or more output modes for the vibrational energy. The one or more output modes for the vibrational energy effect different intravascular lesion-modification procedures with a core wire configured for longitudinal, transverse, or longitudinal and transverse displacement at a distal end of the core wire in accordance with the one or more output modes for the vibrational energy. In some embodiments, the driving-parameter modifier is configured to modify at least the driving parameters selected from pulse repetition frequency, duty cycle, and a combination of the pulse repetition frequency and the duty cycle to effect the different intravascular lesion-modification procedures. In some embodiments, the driving-parameter modifier is configured to modify a pulse repetition frequency between about 5 Hz and 10 Hz to provide transverse displacement of the core wire at a sufficient amplitude to effect atherectomy procedures. In some embodiments, the driving-parameter modifier is configured to modify a duty cycle between about 75% and 100% to provide longitudinal displacement of the core wire at a sufficient amplitude to effect intravascular lesion-crossing procedures.

Also provided herein in some embodiments is a system including a catheter assembly. The catheter assembly includes a sheath, a core wire, and a damping mechanism. The sheath includes a sheath lumen, and the core wire is at least partially disposed within the sheath lumen. The core wire includes a proximal portion and a distal portion of the core wire, wherein the proximal portion of the core wire is coupled to an ultrasound-producing mechanism configured to selectively provide one or more output modes for a vibrational energy. The damping mechanism about the proximal portion of the core wire is configured to dampen transversely oriented vibrational energy in favor of longitudinally oriented vibration energy about the proximal portion of the core wire. A working length of the distal portion of the core wire beyond the sheath is configured for longitudinal, transverse, or longitudinal and transverse displacement in accordance with the one or more output modes for the vibrational energy to effect different intravascular lesion-modification procedures. In some embodiments, the core wire further includes a buckling section within a medial portion of the core wire between the proximal portion and the distal portion of the core wire, wherein the buckling section is configured to produce transverse displacement in the working length of the core wire by buckling in accordance with the one or more output modes for the vibrational energy. In some embodiments, the core wire further includes a tapered section and an inversely tapered section in the medial portion of the core wire, wherein the buckling section is between the tapered section and the inversely tapered section of the core wire, and wherein the buckling section is at least 1" long with a cross-sectional area smaller than either one of the tapered section or the inversely tapered section. In some embodiments, the damping mechanism includes a polymeric sleeve encasing the core wire; a gasket system encasing the polymeric sleeve; and a washer configured to contain the gasket system within a damping-mechanism bore of the catheter assembly. In some embodiments, the gasket system includes a number of radially and longitudinally compressed O-rings configured to prevent irrigation backflow from the catheter assembly into the ultrasound-producing mechanism. In some embodiments, the damping mechanism is centered over a vibrational node of the core wire to minimize frictional heating caused by damping the transversely oriented vibrational energy. In some embodiments, the catheter assembly further includes a guidewire rail including a guidewire-rail lumen externally fixed to the sheath. In some embodiments, the guidewire rail terminates about a distal sheath terminus where the guidewire rail, a guidewire disposed within the guidewire-rail lumen, or a combination of the guidewire rail and a guidewire disposed within the guidewire-rail lumen is free from any effects of transverse displacement of the working length of the core wire.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. An ultrasonic catheter assembly, comprising:
a sheath comprising a sheath lumen;
a core wire at least partially disposed within the sheath lumen, the core wire having a proximal portion and a distal portion, the proximal portion of the core wire configured to be coupled to an ultrasound-producing mechanism, the proximal portion having a first density, the core wire being configured without a separate distal tip;
a working length of the distal portion of the core wire that extends distally from the sheath to a distal end of the core wire, the working length being configured for longitudinal displacement, transverse displacement, or a combination of longitudinal and transverse displacement, in accordance with a plurality of output modes for vibrational energy supplied to the core wire proximal portion by the ultrasound-producing mechanism;
a buckling section between the distal portion and the proximal portion configured to provide localized buckling in the working length of the core wire when outside the sheath and produce transverse displacement of the distal portion from a longitudinal orientation in line with the proximal portion to a transverse orientation that is angularly offset relative to the proximal portion;
a bulked-up portion of the distal portion of the core wire includes the distal end of the core wire; and
a damping mechanism about the proximal portion of the core wire configured to dampen transversely oriented vibrational energy in favor of longitudinally oriented vibrational energy about the proximal portion of the core wire,
wherein a second density of the bulked-up portion is more dense than the first density of the proximal portion of the core wire, the bulked-up portion configured to provide a nodal location for producing longitudinal displacement of the core wire.

2. The ultrasonic catheter assembly of claim 1, wherein the working length of the core wire is in a range between 5 millimeters and 200 millimeters.

3. The ultrasonic catheter assembly of claim 1, wherein the working length of the core wire is in a range between 5 millimeters and 100 millimeters.

4. The ultrasonic catheter assembly of claim 1, wherein the working length of the core wire is in a range between 100 millimeters and 200 millimeters.

5. The ultrasonic catheter assembly of claim 1, wherein when the core wire receives ultrasonic energy from the ultrasound-producing mechanism, a longitudinal displacement of the working length of the core wire results in a micromotion to facilitate cavitation.

6. The ultrasonic catheter assembly of claim 1, wherein when the core wire receives ultrasonic energy from the ultrasound-producing mechanism, a transverse displacement of the working length of the core wire results in a macromotion that facilitates crossing of a lesion.

7. The ultrasonic catheter assembly of claim 1, wherein when the core wire receives ultrasonic energy from the ultrasound-producing mechanism, a longitudinal displacement of the working length of the core wire results in a micromotion and a transverse displacement of the working length of the core wire results in a macromotion, wherein the combination of the micromotion and the macromotion facilitates ablation.

8. The ultrasonic catheter assembly of claim 1, wherein the buckling section is located within a medial portion of the core wire between the proximal portion and the distal portion of the core wire having a reduced diameter compared to the proximal portion and the distal portion.

9. The ultrasonic catheter assembly of claim 1, wherein the buckling section is located between a tapered section of the core wire and an inversely tapered section of the core wire, with a cross-sectional area of the buckling section being smaller than either one of the tapered section or the inversely tapered section.

10. The ultrasonic catheter assembly of claim 1, wherein the buckling section has a length of 1 inch to 4 inches.

11. The ultrasonic catheter assembly of claim 1, wherein the buckling section has a length of 3 inches to 4 inches.

12. The ultrasonic catheter assembly of claim 1, wherein the damping mechanism includes a sleeve that encases the core wire with a first radial compressive force and a gasket system that encases the sleeve with a second radial compressive force.

13. The ultrasonic catheter assembly of claim 1, wherein the damping mechanism includes:
a sleeve encasing the core wire with a first radial compressive force;
a gasket system encasing the sleeve with a second radial compressive force; and
a washer configured to contain the gasket system within a damping-mechanism bore of the ultrasonic catheter assembly.

14. The ultrasonic catheter assembly of claim 1, comprising a guidewire rail having a guidewire-rail lumen, the guidewire rail being externally fixed to the sheath.

15. The ultrasonic catheter assembly of claim 14, wherein the guidewire rail terminates at about a distal sheath terminus, where the working length of the core wire is free to transversely displace without interacting with the guidewire rail.

16. The ultrasonic catheter assembly of claim 14, wherein the guidewire rail terminates about a distal sheath terminus, wherein the guidewire rail, a guidewire disposed within the guidewire-rail lumen, or a combination of the guidewire rail and a guidewire disposed within the guidewire-rail lumen is free from any effects of transverse displacement of the working length of the core wire.

17. An ultrasonic catheter assembly, comprising:
a sheath comprising a sheath lumen;
a core wire at least partially disposed within the sheath lumen, the core wire including a proximal portion, a distal portion, and a buckling section configured to provide localized buckling in a working length of the core wire when outside the sheath and produce transverse displacement of the distal portion from a longitudinal orientation in line with the proximal portion to a transverse orientation that is angularly offset relative to the proximal portion; the distal portion having the working length that extends from the sheath, the proximal portion having a first density, the distal portion having a bulked-up portion that includes a distal end of the core wire, a second density selected from the bulked-up portion, wherein the second density is greater than the first density, the proximal portion of the core wire is coupled to an ultrasound-producing mechanism that produces vibrational energy at a plurality of output modes, the core wire configured to receive the vibrational energy for producing a vibration at the working length, the distal portion configured without a separate distal tip to eliminate surgical procedure-based complications; and
a damping mechanism about the proximal portion of the core wire configured to dampen transversely oriented vibrational energy in favor of longitudinally oriented vibration energy about the proximal portion of the core wire, wherein the working length of the distal portion of the core wire beyond the sheath is configured for longitudinal, transverse, or longitudinal and transverse displacement in accordance with the plurality of output modes of the vibrational energy to effect different intravascular lesion-modification procedures.

18. The ultrasonic catheter assembly of claim 17, wherein the damping mechanism includes:
   a sleeve encasing the core wire with a first radial compressive force;
   a gasket system encasing the sleeve with a second radial compressive force; and
   a washer configured to contain the gasket system within a damping-mechanism bore of the ultrasonic catheter assembly, and
wherein the bulked-up portion of the distal portion is configured to provide a nodal location for producing longitudinal displacement in the core wire.

* * * * *